United States Patent
Yanagisawa et al.

(10) Patent No.: US 6,998,139 B2
(45) Date of Patent: Feb. 14, 2006

(54) BITTERNESS-REDUCED INTRABUCCALLY QUICK DISINTEGRATING TABLETS AND METHOD FOR REDUCING BITTERNESS

(75) Inventors: Masahiro Yanagisawa, Itabashi-ku (JP); Takao Mizumoto, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 10/096,892

(22) Filed: Mar. 14, 2002

(65) Prior Publication Data
US 2003/0039685 A1    Feb. 27, 2003

(30) Foreign Application Priority Data
Mar. 15, 2001    (JP)    .......................... P.2001-074165

(51) Int. Cl.
*A61K 9/00*    (2006.01)
*A61K 9/14*    (2006.01)
*A61K 9/16*    (2006.01)
*A61K 9/20*    (2006.01)
*A61K 9/28*    (2006.01)

(52) U.S. Cl. ...................... 424/465; 424/400; 424/464; 424/474; 424/489; 424/490

(58) Field of Classification Search ................ 424/456, 424/465, 486, 400, 435, 464, 474, 489, 490
See application file for complete search history.

(56) References Cited

U.S. PATENT DOCUMENTS

| 5,576,014 A | 11/1996 | Mizumoto et al. |
| 5,785,984 A | 7/1998 | Kurihara et al. |
| 6,248,357 B1 | 6/2001 | Ohno et al. |
| 6,287,596 B1 | 9/2001 | Murakami et al. |
| 2002/0094345 A1 * | 7/2002 | Abelaira et al. ............ 424/472 |

FOREIGN PATENT DOCUMENTS

| EP | 0 745 382 A1 * | 12/1996 |
| EP | 1 072 256 A1 * | 1/2001 |
| JP | 8-9897 A | 1/1996 |
| WO | WO 99/47124 * | 9/1999 |

* cited by examiner

*Primary Examiner*—Thurman K. Page
*Assistant Examiner*—Simon J. Oh
(74) *Attorney, Agent, or Firm*—Sughrue Mion, PLLC

(57) ABSTRACT

The invention relates to a method for reducing bitterness of bitter drugs, which does not cause delay of release rate, does not show reduction of bioavailability in comparison with conventional pharmaceutical preparations and, due to the use of additives generally used in the field of pharmaceutical preparation, has high practical value, and to intrabuccally quick disintegrating tablets having reduced bitterness of bitter drugs. Illustratively, it relates to an intrabuccally quick disintegrating tablet which comprises a bitter drug and a water-insoluble substance having an average particle size of 30 μm or less, wherein the water-insoluble substance disperses as particles on the tongue surface prior to the release of the bitter drug.

17 Claims, No Drawings

BITTERNESS-REDUCED INTRABUCCALLY QUICK DISINTEGRATING TABLETS AND METHOD FOR REDUCING BITTERNESS

This application is based on Japanese patent application No. 2001-074190 filed Mar. 15, 2001, the entire contents thereof being hereby incorporated by reference.

FIELD OF THE INVENTION

This invention relates to an intrabuccally quick disintegrating tablet in which bitterness of a drug having a bitter taste (to be referred to as bitter drug hereinafter) is reduced and to a method for reducing the bitterness. Particularly, it relates to an intrabuccally quick disintegrating tablet which comprises a bitter drug and a water-insoluble substance having an average particle size of 30 μm or less, wherein (1) a layer containing the water-insoluble substance is arranged on a region where the layer is eluted at an earlier stage than a layer having a bitter taste, or (2) it contains a region having the characteristic of (1), and to a method for reducing the bitterness.

BACKGROUND OF THE INVENTION

Attempts have been made in recent years to apply various drugs to intrabuccally quick disintegrating tablets, but drugs having bitter tastes are limited to only drugs having weak bitterness. Thus, virtually nothing is known about bitterness-reducing techniques which can be generally used for various drugs having bitter tastes, do not spoil characteristics of intrabuccally quick disintegrating tablets and also do not reduce bioavailability.

Bitter drugs are present in many numbers, but when their application to pharmaceutical preparations is considered, it is general to select a method in response to the degree of bitterness of each drug. Illustratively, some methods such as a method in which an additive such as a flavor or a sweetener is added and a film coating method which uses a polymer base are known. According to the method in which a flavor or a sweetener is added, it is difficult to mask bitter tastes by the method alone so that it can be applied to only limited drugs.

Also, the generally known film coating method which uses a polymer base is selected mostly for the purpose of controlling release of drugs. Thus, the significance for selecting this method in reducing bitter tastes of bitter drugs is to control release of a drug in the mouth to a threshold value or less of the drug. The term threshold value as used herein means a limit of drug concentration by which its bitterness is felt, so that the bitterness is not felt when its concentration is lower than this level. Also, in general, a drug having a high threshold value, namely a drug having a high limit concentration by which a bitter taste is felt, can be said that the degree of bitterness is "weak", and a drug having low threshold value can be said that the degree of bitterness is "strong" on the contrary.

However, when a pharmaceutical preparation is obtained by applying the film coating method to a drug having low threshold value, particularly when a pharmaceutical preparation is made into a dosage form such as intrabuccally quick disintegrating tablets which do not accompany taking of water, it is necessary to control amount of the drug to be released in the mouth as small as possible by increasing the coating amount, thus causing a problem as a result that sufficient release of the drug in the digestive tract cannot be secured and bioavailability is reduced in comparison with conventional pharmaceutical preparations.

In addition to these methods, JP-A-6-284866 (corresponds to U.S. Pat. No. 5,785,984) regarding a taste improving agent discloses a protein-lipid complex and JP-A-8-9897 regarding a coating composition of a bitterness-containing substance discloses an acidic phospholipid or its lysate thereof. These inventions take note of the bitterness receiving mechanism carried out by gustatory organ in the mouth and the interaction between a bitter drug and a lipid and describe that these substances are effective in reducing bitter tastes. However, since these substances contain phospholipids, they are unstable to temperature and heat and have a possibility of reducing stability during production or storage of the pharmaceutical preparations, so that their materialization has a difficulty.

Accordingly, the object of the present invention is to provide a method for reducing bitterness of bitter drugs, which does not cause delay of release rate, does not show reduction of bioavailability in comparison with conventional pharmaceutical preparations and, due to the use of additives generally used in the field of pharmaceutical preparation, has high practical value, can be applied to various drugs and does not spoil characteristics of intrabuccally quick disintegrating tablets, and intrabuccally quick disintegrating tablets in which bitter tastes are reduced.

DISCLOSURE OF THE INVENTION

Under such technical levels, the present inventors have take note of bitterness reduction of various substances by their dispersion and retention on the tongue surface and conducted intensive studies on a method which can solve the problems based on this idea. It was found as a result that, when pigments or coloring materials known as dyestuffs, particularly fillers such as titanium oxide, talc and iron oxide generally used in medical preparations, are used, and when a part or entire portion of a pharmaceutical preparation containing these fillers is disintegrated prior to the release of a bitter drug to allow it to disperse as particles and retain on the tongue surface, a water repellent environment is formed on the tongue surface so that reduction of bitter tastes of the bitter drug can be achieved. In addition, the inventors have found that the similar effects can be given when water-insoluble fillers which are generally used in the field of pharmaceutical preparations but have no effects under unground conditions are finely ground to effect pulverization (fine grain formation) and that characteristics of intrabuccally quick disintegrating tablets are not spoiled when they are prepared by this method. The invention has been accomplished based on these findings. Regarding bitter drug-containing pharmaceutical preparations such as tablets or granules, it is a common case to mask bitter tastes by controlling disintegration of pharmaceutical preparations in the mouth as small as possible to effect quick transfer of the pharmaceutical preparations into the digestive tract, but the bitter drug-containing pharmaceutical preparation provided by the present invention is characterized in that its production method contains a step to disintegrate a part or entire portion of a layer containing a water-insoluble filler intentionally in the mouth. Based on an idea which is different from the conventional conception to achieve reduction of bitter tastes by not disintegrate or release bitter drug-containing pharmaceutical preparations in the mouth, the invention intends to reduce bitter tastes of drugs by avoiding certain phenomena such as contact, adsorption and permeation of drugs to or into the tongue through the formation of a water repellent environment which is generated by disintegrating a layer containing a water-insoluble substance in the form of fine particles prior to the release of bitter drugs to allow it to disperse as particles and retain on the tongue surface.

Retaining mechanism of the water-insoluble substance on the tongue surface is not clear yet, based on a result of tests and particle size measurement of effective water-insoluble substances carried out by the inventors, it is considered that particle size of the substance is concerned therein. In addition, the embodiment of the intrabuccally quick disintegrating tablets of the invention was developed to bring out sufficient effect to reduce bitterness of bitter drugs based on a test result that a difference in the time between a bitter drug and a water-insoluble substance appearing in the mouth is concerned in the reduction of bitter taste.

Accordingly, the present invention relates to,

1. In an intrabuccally quick disintegrating tablet which comprises a drug and saccharides, an intrabuccally quick disintegrating tablet which comprises a drug having a bitter taste and a water-insoluble substance having an average particle size of 30 μm or less, wherein (1) a layer containing the water-insoluble substance is arranged on a region where the layer is dissolved at an earlier stage than a drug layer having a bitter taste, or (2) it contains a region having the characteristic of (1), 2. the intrabuccally quick disintegrating tablet according to the item 1, wherein the drag content is from 0.5 to 85% by weight and the water-insoluble substance content is from 5 to 1,000 mg, based on the whole tablet, 3. the intrabuccally quick disintegrating tablet according to the item 2, wherein the water-insoluble substance is one or more substances selected from the group consisting of pharmaceutically acceptable pigments, dyestuffs, metal compounds, cellulose and derivatives thereof, starch and derivatives thereof, natural polymers and derivatives thereof and synthetic polymers, 4. the intrabuccally quick disintegrating tablet according to the item 3, wherein the water-insoluble substance is at least one of titanium oxide and talc, 5. the intrabuccally quick disintegrating tablet according to the item 1, wherein it contains particles having the characteristic, a layer containing the water-insoluble substance is arranged on a region where the layer is dissolved at earlier stage than a drug layer having a bitter taste, 6. the intrabuccally quick disintegrating tablet according to the item 3, wherein the tablet is in the form of a three-layer tablet, 7. the intrabuccally quick disintegrating tablet according to the item 1, wherein the saccharides are granulated product prepared by using saccharides having low moldability spraying saccharides having high moldability as a binder, thereby effecting at least one of coating and granulating, 8. the intrabuccally quick disintegrating tablet according to the item 7, wherein the production process contains humidification and drying steps, 9. the intrabuccally quick disintegrating tablet according to the item 8, wherein the saccharides having low moldability are one or more saccharides selected from lactose, mannitol, glucose, sucrose, xylitol and erythritol, 10. the intrabuccally quick disintegrating tablet according to the item 8, wherein the saccharides having high moldability are one or more saccharides selected from maltose, maltitol, sorbitol and trehalose, 11. use of the intrabuccally quick disintegrating tablet described in the item 8 for reducing bitterness in the mouth, which is effected by dispersing and retaining a water-insoluble substance having an average particle size of 30 μm or less as particles on the tongue surface prior to release of a drug having a bitter taste, 12. the use of intrabuccally quick disintegrating tablet according to the item 10, wherein the saccharides having low moldability are one or more saccharides selected from lactose, mannitol, glucose, sucrose, xylitol and erythritol, 13. the use of intrabuccally quick disintegrating tablet according to the item 10, wherein the saccharides having high moldability are one or more saccharides selected from maltose, maltitol, sorbitol and trehalose, 14. the use of intrabuccally quick disintegrating tablet according to the item 10, wherein the water-insoluble substance is one or more substances selected from the group consisting of pharmaceutically acceptable pigments, dyestuffs, metal compounds, cellulose and derivatives thereof, starch and derivatives thereof, natural polymers and derivatives thereof and synthetic polymers, and 15. the use of intrabuccally quick disintegrating tablet according to the item 14, wherein the water-insoluble substance is at least one of titanium oxide and talc.

Other objects and advantages of the present invention will be made apparent as the description progresses.

The term "intrabuccally quick disintegrating tablets" as used herein means those which are disclosed, e.g., in International Publication WO 98/02185 (corresponds to U.S. Pat. No. 6,287,596), International Publication WO No. 95/20380 (corresponds to U.S. Pat. No. 5,576,014) and JP-A-10-182436 (corresponds to U.S. Pat. No. 6,248,357), illustratively those which are disintegrated in the mouth within 2 minutes, preferably within 1 minute.

The term "water-insoluble substance" as used herein means a water-insoluble solid substance which is a pharmaceutical preparation material generally used in the field of medical oral preparations. Its examples are water-insoluble solid substances described in The Pharmacopoeia of Japan (13th edition, Hirokawa Shoten) and Dictionary of Pharmaceutical Additives (recommended by Examination Division, Pharmaceutical Affairs Bureau, Ministry of Health and Welfare, edited by Japan Pharmaceutical Additives Association). Also, the term "water-insoluble" corresponds to a term "hardly soluble" described in The Pharmacopoeia of Japan, General Rules, regarding solubility, namely a property to require 10,000 ml or more of a solvent for dissolving 1 g of a solute among dissolving degrees within 30 minutes when vigorously stirred at 20±5° C. for 30 seconds at 5 minute intervals.

Also, the term "average particle size" is average particle size of primary particles of the filler and means a value obtained by a laser diffraction type particle distribution analyzer generally used for the measurement of average particle size (e.g., HORIBA Laser Diffraction/Scattering Particle Distribution Analyzer). According to the present invention, among average particle sizes of a filler calculated based on this method, those having 30 μm or less are defined as fine powder (fine particles), and those exceeding 30 μm as large particles.

Also, the term "prior to the release of bitter drug" means that the time when disintegration and dispersion of a layer containing the water-insoluble substance start is earlier than the time when release of a bitter drug starts. Illustratively, it is desirable that release of a bitter drug starts 1 to 10 seconds, preferably 5 to 10 seconds, after commencement of the disintegration and dispersion of a layer containing the water-insoluble substance, so that as an illustrative example of the term "prior to the release of bitter drug", it is desirable that the disintegration and dispersion of a layer containing the water-insoluble substance start "1 to 10 seconds before the release of bitter drug". Regarding the description "disintegration, dispersion and retention on the tongue surface", it is not necessary to occur these processes stepwise, and disintegration and dispersion on the tongue surface, or dispersion on the tongue surface and retention, may occur simultaneously.

Regarding retention on the tongue surface, factors having close relation to the retention property are not clear yet, but it is considered that particle size of the water-insoluble substance is one of factors. Accordingly, the term "as particles" means it becomes a state of powder or primary particles in the mouth and shows that they are the best mode for bringing out effects of the water-insoluble substance of 30 µm or less. Also, a period of time until a bitter drug reaches the stomach is necessary as the retention time of the water-insoluble substance on the tongue surface, which is from 1 to 5 minutes, preferably from 2 to 5 minutes, more preferably from 3 to 5 minutes. Such a mode shows considerable effects when applied not only to pharmaceutical preparations which are taken with water but particularly to intrabuccally quick disintegrating tablets which are not taken with water. In addition, usual bitterness reducing methods require adjustment of the amount of fillers in response to the bitterness and amount of drugs (e.g., amount of film coating), but according to the present invention, it is not necessary to adjust amount of the water-insoluble substance in response to the bitterness and amount of drugs, and it may be in such an amount that it is sufficiently dispersed on the tongue surface, e.g., it may be from 5 to 1,000 mg, preferably from 10 to 500 mg, more preferably from 20 to 250 mg.

Also, the term "does not show reduction of bioavailability" in comparison with conventional pharmaceutical preparations, as used herein, means that when compared with delay of general pharmaceutical preparations (or release of a bitter drug itself), delay of release is not shown in an in vitro dissolution test so that it is predicted that its releasing property in vivo is also indirectly guaranteed showing no reduction of bioavailability.

The term "does not spoil characteristics of intrabuccally quick disintegrating tablets" as used herein means that when the techniques of the present invention are applied to intrabuccally quick disintegrating tablets, the intrabuccally quick disintegrating tablets show a hardness of 2 kp or more and their disintegration time in the mouth is within 2 minutes.

The water-insoluble substance to be used in the invention is not particularly limited with the proviso that it is a water-insoluble solid substance having an average particle size of 30 µm or less, preferably 20 µm or less, more preferably 10 µm or less, which is pharmaceutically acceptable and can achieve the object of the present invention. The lower limit of the average particle size is not particularly limited, but the average particle size is preferably 0.01 µm or more, more preferably 0.1 µm or more. Its examples include water-insoluble materials frequently used in conventional pharmaceutical preparations, such as pigments, coloring agents, metal compounds, cellulose and derivatives thereof, starch and derivatives thereof, natural polymers and derivatives thereof and synthetic polymers. Particularly, pigments and coloring agents are water-insoluble materials most suited for the invention. Also, as occasion demands, it can be adjusted to a desired particle size by pulverizing it using an appropriate pulverizer such as hammer mill, sample mill or jet mill, or by dissolving the water-insoluble substance in an appropriate solvent and then spray-drying the solution.

Examples of the pigment preferred as the water-insoluble substance include color pigments such as iron sesquioxide, white pigments such as titanium oxide and extender pigments such as talc, kaolin, calcium carbonate and magnesium carbonate, of which iron sesquioxide, titanium oxide and talc are more preferred. Titanium oxide can be exemplified as particularly suitable pigment, because it is advantageous in achieving the object of the present invention due to its excellent dispersing ability and retaining ability in the mouth and production workability.

Examples of the coloring agent include yellow iron sesquioxide and Yellow No. 4 aluminum lake, of which yellow iron sesquioxide is particularly preferred.

A metal compound of the water-insoluble material can be used by making the metal compound into a gel form, and illustrative examples the most preferred metal compounds include aluminum compounds such as dry aluminum hydroxide gel, synthetic aluminum silicate, aluminum magnesium hydroxide and aluminum hydroxide gel, calcium compounds such as calcium silicate and calcium stearate, magnesium oxide, magnesium silicate, magnesium stearate and silicic acid compounds such as soft silicic anhydride and synthetic hydrotalcite. Particularly preferred is dry aluminum hydroxide gel.

As a cellulose and derivatives thereof, crystalline cellulose, ethyl cellulose, hydroxypropylmethylcellulose acetate succinate and carboxymethylethylcellulose can be cited as particularly preferred examples.

As a starch and derivatives thereof, corn starch and potato starch can be cited as particularly preferred examples.

As a natural polymer and derivatives thereof, gelatin and shellac can be cited as particularly preferred examples.

Examples of the synthetic polymer include methacrylic acid copolymers L and S, aminoalkyl methacrylate copolymers E and RS and dimethylpolysiloxane.

As the water-insoluble substance, one or two or more of the substances shown herein can be used by an optional combination. Mixing amount of water-insoluble substances is as defined in the foregoing.

The drug to be used in the present invention is not particularly limited with the proviso that it is used as a medically active component and shows a bitter taste at a limit concentration by which bitterness is felt, namely exceeding its threshold value, in an effective amount per pharmaceutical preparation unit. Examples of such a medically active component include central nervous system drugs such as a hypnotic sedative, a sleep inductor, an anxiolytic drug, an antiepileptic, an antipyretic-analgesic-anti-inflammatory drug, an antidepressant, an antiparkinsonism drug and a psychoneurosis drug, circulatory drugs such as a skeletal muscle relaxant, an autonomic drug, an antispasmodic agent, a cardiotonic agent, an arrhythmia drug, a diuretic agent, an antihypertensive drug, a vasoconstrictor, a coronary vasodilator, a peripheral vasodilator and a hyperlipemia drug, allergy drugs such as an antitussive expectorant and a bronchodilator, digestive organ drugs such as an antidiarrheal drug, a drug for controlling intestinal function, an antiulcer drug, a stomatic digestive drug and an antacid agent and hormone drugs such as a pituitary hormone drug, a thyroid hormone drug and an anti-thyroid hormone drug, as well as a urogenital organ drug, a vitamin compound, a hemostatic drug, a blood coagulation inhibitor, a pulmonary disease drug, an antidote, a habitual intoxication drug, a gout treating drug, a diabetic drug, an anti-malignant tumor drug, an antihistaminic drug, a crude drug, a Chinese orthodox medicine, an antibiotic, a chemotherapy drug, an anthelmintic drug and an anti-protozoan drug. Illustratively, meclofenoxate hydrochloride, chloramphenicol, aminophylline, erythromycin, josamycin, calcium hopantenate, phenobarbital, cimetidine, famotidine, etilefrine hydrochloride, diltiazem hydrochloride, propranolol hydrochloride, flufenamic acid, atolvastatin calcium, digitoxin, theophylline, promethazine hydrochloride, quinine hydrochloride, sulpyrine and ibuprofen can be exemplified. In addition, the drug can also be used alone or by optionally combining two or more of them Mixing amount of the drug is optionally selected generally in response to the kind of drugs or medical use (indication), though not particularly limited with the proviso that it is a therapeutically effective amount or a prophylactically effective amount. The amount is preferably from 0.5 to 85% by weight, more preferably from 0.5 to 80% by weight, based on the whole pharmaceutical preparation. More preferably, it is from 0.5 to 50% by weight, most preferably from 0.5 to 10% by weight.

Form of the pharmaceutical preparation of the invention is not particularly limited and can be applied to various dosage forms generally used as medicament, but it is necessary to consider a form which can disintegrate, disperse and retain a layer containing the water-insoluble substance on the tongue surface prior to the release of a bitter drug. Also, it is necessary that the water-insoluble substance is dispersed as particles in the mouth, namely it returns into a state of powder or primary particles. In the case of a physical mixture of a bitter drug and the water-insoluble substance, drug particles and water-insoluble substance particles reach the gustatory cells at the same time so that sufficient bitterness control cannot be achieved, but according to the formulation disclosed by the present invention, the bitterness control is achieved by the water repellent environment formed by the fine particle water-insoluble substance existing as powder or primary particles. As illustrative dosage forms, three-layer tablets in which the upper and lower layers contain the water-insoluble substance and the intermediate layer contains a bitter drug, dry coated tablets in which the outer layer part contains the water-insoluble substance and the core part contains a bitter drug, particles or granules in which a water-insoluble substance layer is laminated or coated on the core part containing a bitter drug or solid preparations such as dry syrups, capsules, tablets, troches and chewable tablets in which the granules are contained by a known method can be considered, and the object of the present invention is achieved by dispersion of the water-insoluble substance as fine particles contained in the pharmaceutical preparation, namely its returning to a state of powder or primary particles, when these pharmaceutical preparations are administered into the mouth. Also, it can be made into intrabuccally quick disintegrating tablets in accordance with the method of International Publication No. 95-20380. Illustratively, intrabuccally quick disintegrating tablets containing saccharides are preferred embodiment, and they can be prepared using a granulated product obtained by a method in which the granulated product is prepared by using saccharides having low moldability spraying saccharides having high moldability as a binder, thereby effecting at least one of coating and granulating.

The term "saccharides having low moldability" as used herein means, e.g., that when 150 mg of saccharides are made into tablets using a punch of 8 mm in diameter under a tablet making pressure of from 10 to 50 kg/cm$^2$, the tablets show a hardness of from 0 to 2 kp, and the term "saccharides having high moldability" means that the hardness by the same method shows 2 kp or more. The saccharides having low moldability are those which are pharmaceutically acceptable, and their examples include lactose, mannitol, glucose, sucrose, xylitol and erythritol. It is possible to use them alone or by optionally combining two or more of them.

The saccharides having high moldability are those which are pharmaceutically acceptable, and their examples include maltose, maltitol, sorbitol and trehalose. It is possible also to use these saccharides alone or by optionally combining two or more of them.

In addition, in order to improve hardness of the thus prepared tablets, humidification and drying steps can be employed. The "humidification" is determined by apparent critical relative humidity of the saccharides to be contained, but they are humidified generally to the critical relative humidity or more. For example, it is from 30 to 100 RH %, preferably from 50 to 90 RH %, as humidity. In this case, the temperature is preferably from 15 to 50° C., more preferably from 20 to 40° C. The treating time is from 1 to 36 hours, preferably from 12 to 24 hours. The "drying" is not particularly limited with the proviso that it is a step to remove moisture absorbed by the humidification. For example, a drying temperature condition of from 10 to 100° C., preferably from 20 to 60° C., more preferably from 25 to 40° C., can be set. The treating time can be set to a period of from 0.5 to 5 hours, preferably from 1 to 3 hours.

In obtaining the pharmaceutical preparation of the present invention, known methods can be used and one and/or two or more of conventionally used additives can be used by optionally combining them. Examples of such additives include binders, disintegrating agents, thickeners, fillers, excipients, lubricants, correctives and aromatics. Also, depending on the water-insoluble substance used, the tongue surface becomes a colored state after taking of the product of the present invention due to the substance's color, and it is possible to make a desired color by optionally adding a water-soluble dye such as Food Dye Blue No. 1, Food Dye Yellow No. 4, Food Dye Yellow No. 5, Food Dye Red No. 102, Food Dye Red No. 2 or Food Dye Red No. 3 as occasion demands.

In the case of three-layer tablets, a technique is known for controlling bitterness by positioning a bitter drug on the intermediate second layer, but the present invention has a completely different technical idea because almost all of the components constituting the tablets disintegrate in the mouth.

Next, the production method of the present invention is described.

A drug is made into primary granules by mixing it with a filler such as corn starch, making the mixture into granules using, e.g., hydroxypropylcellulose (HPC-SL) and then blending with an additive agent such as a disintegrating agent. When made into intrabuccally quick disintegrating tablets, a drug is mixed with a saccharide having low moldability such as mannitol and then made into granules using a saccharide having high moldability such as maltose as a binder (primary granules). On the other hand, lactose or corn starch is made into granules in the same manner as the case of primary granules and mixed with the water-insoluble substance shown by the invention to obtain secondary granules. In the case of intrabuccally quick disintegrating tablets, mannitol, e.g., is made into granules using, e.g., maltose, and then mixed with the water-insoluble substance to obtain secondary granule. When three-layer tablets are desired, the secondary granules are used as the first and third layers and the primary granules are used as the second layer and they are made into tablets using a three-layer tablet making machine. Also, when dry coated tablets are desired, the primary granules are made into core tablets in advance and then the secondary granules are used as the outer layer to make final tablets using a dry coated tablet making machine.

The tablets produced by this method are orally administered, a part or entire portion of the layer containing the water-insoluble substance is disintegrated in the mouth, and simultaneously or thereafter, the water-insoluble substance is dispersed or retained as particles on the tongue surface. Accordingly, the tongue surface becomes a water repellent environment under such a state. After passing this stage, the layer containing a bitter drug is disintegrated keeping the water-insoluble substance-retaining state and transferred into the digestive tract, thereby achieving the bitterness reducing method of the present invention.

The present invention exerts considerable effects from the viewpoint that it rendered possible provision of intrabuccally quick disintegrating tablets having reduced bitterness of bitter drugs, which do not cause delay of release rate, do not show reduction of bioavailability in comparison with conventional pharmaceutical preparations and, because additives generally used in the field of pharmaceutical preparation can be used, have excellent stability and workability and also have markedly high practical value.

BEST MODE FOR CARRYING OUT THE INVENTION

The following describes the present invention further in detail with reference to examples, though the present invention is not limited thereto. In this connection, measurement of average particle size, evaluation of bitterness, measurement of the hardness of intrabuccally quick disintegrating tablets and measurement of disintegration time in the mouth used in the examples were carried out by the following test methods.

Measurement of Average Particle Size

Each sample to be measured (roughly from 30 to 50 mg) is put on a micro-spatula, dispersed in an appropriate dispersion medium in which the sample is not dissolved (e.g., n-hexane or water) and then measured using a HORIBA laser diffraction/scattering particle distribution analyzer (HORIBA, LA-910). The results are automatically analyzed by a computer.

Test Method for Evaluating Bitterness

Prior to the test, each member of a panel rinses out the mouth thoroughly with water.

(1) When a water-insoluble substance is dispersed on the tongue in advance, the water-insoluble substance in an amount shown in each example is put on the tongue and dispersed, and 3 seconds thereafter, a drug solution is held in the mouth for 3 seconds and then spit out. Thereafter, the mouth is rinsed thoroughly with water.

(2) When a suspension prepared by suspending a water-insoluble substance in a drug solution is evaluated, the suspension is held in the mouth for 3 seconds and then spit out, and then the mouth is rinsed thoroughly with water.

(3) In the case of the evaluation of tablets, a tablet is held in the mouth until it is disintegrated (roughly 20 seconds) and then spit out, and the mouth is rinsed thoroughly with water.

The degree of bitterness when a solution or a tablet is held in the mouth is shown by the following symbols. –: bitterness is not felt, ±: bitterness is hardly felt, +: bitterness is felt but bearable, ++: bitterness is felt and unbearable.

Also, when the same member of the panel repeats the test, the test is carried out after sufficient period of time so that taste of the prior test does not remain (at least 1 hour or more).

Measurement of Hardness of Intrabuccally Quick Disintegrating Tablets

This is measured using Schleuninger tablet hardness meter (mfd. by Schleuninger). The test is carried out using three tablets and shown by their average value. The hardness of tablet shows a force required for crushing each tablet (unit, kp).

Measurement of Disintegration Time in the Mouth

A period of time after holding a tablet until in the mouth until it is completely disintegrated in the mouth is measured.

EXAMPLE 1

A 50 mg portion of titanium oxide (relevant to The Pharmacopoeia of Japan) was dispersed on the tongue in advance and then 5 ml of 20 mM theophylline (mfd. by Nakalai Tesque) aqueous solution was held in the mouth to evaluate its bitterness by healthy persons (n=2) (Table 1).

EXAMPLE 2

A 50 mg portion of talc (relevant to The Pharmacopoeia of Japan, mfd. by Kihara Kasei) was dispersed on the tongue in advance and then 5 ml of 20 mM theophylline (mfd. by Nakalai Tesque) aqueous solution was held in the mouth to evaluate its bitterness by healthy persons (n=2) in the same manner as in Example 1 (Table 1).

EXAMPLE 3

A 50 mg portion of dry aluminum hydroxide gel (relevant to The Pharmacopoeia of Japan, mfd. by Kyowa Kagaku) was dispersed on the tongue in advance and then 5 ml of 20 mM theophylline (mfd. by Nakalai Tesque) aqueous solution was held in the mouth to evaluate its bitterness by healthy persons (n=2) in the same manner as in Example 1 (Table 1).

COMPARATIVE EXAMPLE 1

A 50 mg portion of titanium oxide (relevant to The Pharmacopoeia of Japan) was dispersed in 5 ml of 20 mM theophylline (mfd. by Nakalai Tesque) aqueous solution and then held in the mouth to evaluate its bitterness by healthy persons (n=2) (Table 1).

COMPARATIVE EXAMPLE 2

A 50 mg portion of talc (relevant to The Pharmacopoeia of Japan, mfd. by Kihara Kasei) was dispersed in 5 ml of 20 mM theophylline (mfd. by Nakalai Tesque) aqueous solution and then held in the mouth to evaluate its bitterness by healthy persons (n=2) (Table 1).

COMPARATIVE EXAMPLE 3

A 50 mg portion of dry aluminum hydroxide gel (relevant to The Pharmacopoeia of Japan, mfd. by Kyowa Kagaku) was dispersed in 5 ml of 20 mM theophylline (mfd. by Nakalai Tesque) aqueous solution and then held in the mouth to evaluate its bitterness by healthy persons (n=2) (Table 1).

TABLE 1

Effect of various dispersed fillers to control
bitterness of theophylline aqueous solution

|  |  | Panelist | |
|---|---|---|---|
|  |  | 1 | 2 |
| Example 1 | Titanium oxide | − | − |
| Example 2 | Talc | − | − |
| Example 3 | Dry aluminum hydroxide gel | − | − |
| Comparative Example 1 | Titanium oxide | ++ | ++ |
| Comparative Example 2 | Talc | ++ | ++ |
| Comparative Example 3 | Dry aluminum hydroxide gel | ± | + |

Discussion

As a result, it was considered that the reduction of bitterness by the water-insoluble substances is not due to their dilution effect but evidently due to their spread on the tongue surface precedent to the bitter drug.

TEST EXAMPLE 1

When average particle sizes of these fillers were measured, the following results were obtained.

TABLE 2

Average particle sizes of fillers

| Fillers | Average particle size ($\mu$m) |
|---|---|
| Titanium oxide | 0.4 |
| Talc | 7.3 |
| Dry aluminum hydroxide gel | 3.2 |

Discussion

It was confirmed from these results that the water-insoluble substances used are fine particles.

EXAMPLE 4

When Cumulite (an aluminum hydroxide/sodium bicarbonate coprecipitation product, mfd. by Kyowa Kagaku, measured average particle size 72 $\mu$m) was thoroughly pulverized in a mortar and average particle size was measured, it was about 9 $\mu$m. Evaluation of bitterness of the un-pulverized and mortar-pulverized Cumulite samples was carried out (Table 3).

TABLE 3

Influence of particle sizes of Cumulite on the
bitterness of theophylline aqueous solution

|  | Panelist | |
|---|---|---|
|  | 1 | 2 |
| Cumulite (72 $\mu$m) | + | + |
| Pulverized Cumulite (9 $\mu$m) | − | ± |

Discussion

From the above results, a possibility was suggested that bitterness of drugs can be reduced by allowing a fine particle water-insoluble substance to disperse and retain in advance on the tongue surface as particles.

EXAMPLE 5

Evaluation of bitterness of a drug solution was carried out by the following three methods using each of the fillers shown below. Also, average particle size of each filler was measured (Table 4). (1) A water-insoluble substance is dispersed in 5 ml of 20 mM theophylline aqueous solution and bitterness of the suspension is evaluated, (2) a water-insoluble substance is dispersed on the tongue in advance and bitterness of 5 ml of 20 mM theophylline aqueous solution is evaluated, (3) a water-insoluble substance is pulverized using a jet mill (mfd. by Hosokawa Micron) and the evaluation is carried out in the same manner as (2) using the pulverized sample.

TABLE 4

Difference in the degree of bitterness control by
different evaluation methods of fillers, and average
particle sizes thereof

|  | Method (1) | | Method (2) | | | Method (3) | | |
|---|---|---|---|---|---|---|---|---|
|  | Panelist | | Panelist | | Average particle size ($\mu$m) | Panelist | | Average particle size ($\mu$m) |
|  | 1 | 2 | 1 | 2 |  | 1 | 2 |  |
| Ethyl cellulose | ± | + | + | + | 60.0 | − | − | 11.5 |
| HPMC-AS | ± | + | − | ± | 17.8 | − | ± | 7.8 |
| Corn starch | + | ++ | − | ± | 24.0 | − | ± | 13.2 |
| Theolus | ++ | ++ | ± | + | 65.1 | − | ± | 13.5 |

Discussion

It is considered from the above results that the particle size effective in controlling bitterness is about 30 $\mu$m or less.

EXAMPLE 6

Granules were obtained by granulating 380 g of mannitol (Towa Kasei) with an aqueous solution containing 20 g of maltose (Hayashibara, SunMalto Midori) using a fluidized bed granulating machine (mfd. by Ohgawara Kakoki, UNI-GLATT). A 80 mg portion of the granules and 20 mg of titanium oxide (Freund Sangyo, official grade) were weighed, mixed, packed in a die of 9 mm in diameter and then lightly pressed with a punch to obtain a first layer. A 20 mg portion of theophylline (mfd. by Nakalai Tesque) and 80 mg of the granules were weighed, mixed, packed on the first layer and then lightly pressed with a punch to obtain a second layer. A mixture having the same composition of the first layer was prepared, packed on the second layer and then compressed with a punch to obtain 300 mg in total of intrabuccally quick disintegrating three-layer tablets (an oil press was used). Separately, a filler having the same composition of the intrabuccally quick disintegrating three-layer tablets and the granules were weighed, mixed and then made into tablets with oil press using a punch of 9 mm in diameter to obtain control intrabuccally quick disintegrating tablets. Bitterness of the thus obtained three-layer tablets and control tablets was evaluated. In this connection, hardness of the three-layer tablets was 4 kp, and their disintegration time in the mouth was 25 seconds.

TABLE 5

Comparison of bitterness of three-layer tablets
and control tablets

| | Panelist | |
|---|---|---|
| | 1 | 2 |
| Three-layer tablets | − | ± |
| Control tablets | + | ++ |

EXAMPLE 7

A 30 g portion of josamycin (Yamanouchi Pharmaceutical Co., Ltd.) was added to a mixed solution of 90 g of aquacoat (Asahi Chemical Industry, ECD-30) and 3 g of triacetin (Yuki Gosei Kogyo, non-official grade) and uniformly dispersed. This suspension was spray-dried using a spray dryer (Ohgawara Kakoki, type L-8) to obtain spherical granules. A 100 mg portion of the granules shown in Example 6 and 30 mg of titanium oxide (Freund Sangyo, official drug) were mixed to be used as a first layer of three-layer tablets. Also, 100 mg of the spherical granules were weighed and mixed with 100 mg of the granules shown in Example 6 and used as a second layer and then finally using a mixture of 100 mg of the granules shown in Example 6 and 30 mg of titanium oxide as a third layer, 460 mg in total of intrabuccally quick disintegrating three-layer tablets were prepared by oil press. The three-layer tablets showed a hardness of 3 kp and an oral disintegration time of 22 seconds.

COMPARATIVE EXAMPLE

A 50 mg portion of Josamycin was weighed and mixed with the same fillers of the composition of three-layer tablets (all fillers excluding the spherical granules), and then 410 mg in total of tablets were prepared by oil press and used as control tablets.

TABLE 6

Comparison of bitterness of three-layer tablets
and control tablets

| | Panelist | |
|---|---|---|
| | 1 | 2 |
| Three-layer tablets | − | − |
| Control tablets | ++ | ++ |

Discussion

It was considered from Examples 6 and 7 that the bitterness was controlled due to dispersion of titanium oxide on the tongue surface prior to the release of the drug. It was confirmed also that characteristics of the intrabuccally quick disintegrating tablets are not spoiled.

EXAMPLE 8

A mixture of aquacoat (Asahi Chemical Industry, ECD-30) and triacetin (Yuki Gosei Kogyo, non-official grade) (compositional ratio, 9:1) was coated on the spherical granules shown in Example 7 in a coating amount of 5% using a fluidized bed granulating machine (Glatt GmbH, GPCG).

Next, a mixed solution of titanium oxide (Freund Sangyo, official drug), aquacoat and triacetin (compositional ratio, 9:0.9:0.1) was coated on the granules in a coating amount of 40% to prepare titanium oxide-coated granules. Using 500 ml of the dissolution test first solution of The Pharmacopoeia of Japan, dissolution test (paddle method, 100 rpm) of the granules and titanium oxide-un-coated granules (prepared by coating the spherical granules shown in Example 7 with aquacoat and triacetin in a coating amount of 5%, used as a comparative example) was carried out to find that both showed the same dissolution. Bitterness of both of them was evaluated.

TABLE 7

Comparison of bitterness of titanium oxide-coated
granules and comparative example

| | Panelist | |
|---|---|---|
| | 1 | 2 |
| Coated granules | ± | ± |
| Comparative example | + | + |

Discussion

The titanium oxide-coated granules reduced the bitterness despite the same dissolution with the comparative example in vitro. Thus, it was considered that the reduction of bitterness by this pharmaceutical preparation was achieved by dispersion of the titanium oxide layer on the tongue surface without causing reduction of bioavailability.

While the invention has been described in detail and with reference to specific embodiments thereof, it will be apparent to one skilled in the art that various changes and modifications can be made therein without departing from the scope thereof.

What is claimed is:

1. An intrabucally quick disintegrating dosage form selected from the group consisting of:
   (a) a dry-coated tablet which comprises:
      (i) an outer layer comprising at least one saccharide and a water-insoluble pharmaceutically and/or coloring agent in the form of particles having an average particle size of 30 μm or less and in an amount of from 20 to 250 mg per tablet, and
      (ii) an inner layer or a core comprising a drug having a bitter taste and at least one saccharide, wherein said inner layer or said core is disposed at a position within said outer layer;
   (b) laminated or coated granules which comprise:
      (i) a core comprising a drug having a bitter taste and at least one saccharide, and
      (ii) an outer layer laminated or coated thereon and comprising at least one saccharide and a water-insoluble pharmaceutically acceptable pigment and/or coloring agent in the form of particles having an average particle size of 30 μm or less and in an amount of from 20 to 250 mg per dosage form, wherein said granules are or are not contained in a solid preparation; and
   (c) a three-layered tablet which comprises:
      an upper and lower layer, each comprising at least one saccharide and a water-insoluble pharmaceutically acceptable pigment and/or coloring agent in the form of particles having an average particle size of 30 μm or less and in an amount of from 20 to 250 mg per tablet, arranged on an intermediate layer which comprises a drug having a bitter taste and at least one saccharide, wherein when the dosage form is taken in the mouth, said water-insoluble pharmaceutically acceptable pigment and/or coloring agent is dispersed as particles and the dispersion of the particles starts 1 to 10 seconds prior to release of the drug having the bitter taste.

2. The intrabucally quick disintegrating dosage form according to claim 1, wherein the drug content is from 0.5 to 85% by weight based on the whole dosage form.

3. The intrabucally quick disintegrating dosage form according to claim 2, which is said three-layered tablet.

4. The intrabuccally quick disintegrating dosage form according to claim 1, wherein the pigment and/or coloring agent is at least one of titanium oxide or talc.

5. The intrabuccally quick disintegrating dosage form according to claim 1, wherein at least one saccharide is a granulated product prepared by spraying, coating and/or granulating a saccharide having low moldability with a saccharide having high moldability.

6. The intrabuccally quick disintegrating dosage form according to claim 5, wherein the production process contains humidification and drying steps.

7. The intrabuccally quick disintegrating dosage form according to claim 6, wherein the saccharide having low moldability is one or more saccharides selected from the group consisting of lactose, mannitol, glucose, sucrose, xylitol and erythritol.

8. The intrabuccally quick disintegrating dosage form according to claim 6, wherein the saccharide having high moldability is one or more saccharides selected from the group consisting of maltose, maltitol, sorbitol and trehalose.

9. The intrabuccally quick dosage form according to claim 1, which is said three-layered tablet.

10. The intrabuccally disintegrating dosage form according to claim 1, wherein the dry-coated tablet comprises an outer layer containing the pigment and/or coloring agent and a core containing the drug.

11. The intrabuccally disintegrating dosage form according to claim 1, wherein the granules are contained in a solid preparation which is a monolithic tablet.

12. A method for reducing bitterness in the mouth when administering a bitter drug, said method comprising orally administering the intrabuccally quick disintegrating dosage form of claim 1, and wherein said method is effected by dispersing and retaining as particles the pigment and/or coloring agent on the tongue surface prior to release of the drug having a bitter taste.

13. The method according to claim 12, wherein at least one saccharide is a granulated product prepared by spraying, coating and/or granulating a saccharide having low moldability with a saccharide having high moldability.

14. The method according to claim 13, wherein the production process contains humidification and drying steps.

15. The method according to claim 14, wherein the saccharide having low moldability is one or more saccharides selected from the group consisting of lactose, mannitol, glucose, sucrose, xylitol and erythritol.

16. The method according to claim 14, wherein the saccharide having high moldability is one or more saccharides selected from the group consisting of maltose, maltitol, sorbitol and trehalose.

17. The method according to claim 12, wherein the water-insoluble substance is at least one member selected from the group consisting of titanium oxide and talc.

* * * * *